United States Patent [19]

Williams

[11] Patent Number: Plant 5,271

[45] Date of Patent: Aug. 14, 1984

[54] MINIATURE ROSE PLANT—WILDAK VARIETY

[75] Inventor: J. Benjamin Williams, Silver Spring, Md.

[73] Assignee: The Conard-Pyle Company, West Grove, Pa.

[21] Appl. No.: 393,865

[22] Filed: Jun. 30, 1982

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Burns, Doane, Swecker & Mathis

[57] ABSTRACT

A new and distinct variety of Miniature rose plant is provided having highly attractive double flowers which exhibit a blend of orange and yellow tones. The new variety resulted from the crossing of the Zorina variety (U.S. Plant Pat. No. 2,321) and the Starina variety (U.S. Plant Pat. No. 2,646). The buds of the new variety are perfectly formed and blossom into gracefully shaped blooms of approximately one and one-half inches. The variety also forces well and performs well outdoors.

2 Drawing Figures

SUMMARY OF THE INVENTION

The object of the present invention is to provide a new variety of rose plant of the Miniature Class which is distinguished from prior varieties by the following combination of characteristics:

(a) from the physical standpoint the plant with medium green adult wood has a semi-erect growth habit, forms dark green glossy leaves, and forms double flowers which exhibit a blend of orange and yellow tones with a pinkish accent at the flower center; and (b) from the biological standpoint the plant has vigorous and regular vegetation, exhibits an abundant and repeated florescence, exhibits the ability to grow well in the greenhouse or outside, possesses the ability for its blossoms to last for a long time, and forms petals which detach cleanly.

In view of these characteristics the new variety meets the needs of the horticultural industry and is particularly suited for ornamental use in gardens and forcing as a pot plant.

The new variety resulted from artificial pollination with the variety Zorina (U.S. Plant Pat. 2,321) serving as the seed parent, and the variety Starina (U.S. Plant Pat. No. 2,646) serving as the pollen parent.

The characteristics and properties of this new variety have been found to be transmissible by vegetative propagation through softwood cuttings, grafting and budding performed at West Grove, Pa.

The rose plant of the new variety has been named the Wildak variety. Plants of this new variety presently are being marketed by the Conard-Pyle Co. of West Grove, Pa. under the AMBER FLASH trademark and are members of a family of Miniature rose plants which presently are being marketed by such company under the MINIFLORA trademark.

BRIEF DESCRIPTION OF THE PHOTOGRAPHS

The accompanying photographs show as nearly true as it is possible to make the same in color illustrations of this character, typical specimens of plant parts from two year old plants produced from softwood cuttings and growing in the open air during mid-June at West Grove, Pa.

In FIG. 1 are shown blossoms of the new variety in various stages of opening.

In FIG. 2 are shown various plant parts of the new variety. In the far left portion of the photograph is shown foliage and a cluster of buds in different stages of development wherein in some instances the sepals have begun to open. In the upper left center portion of the photograph is shown a segment of a main branch. In the upper center portion of the photograph is shown a segment of a flowering stem. In the right portion of the photograph are shown blossoms in various stages of opening. In the middle lower right portion of the photograph is shown a bud immediately following the opening of the sepals. In the lower portion of the photograph are shown a leaf with five leaflets (center) and a leaf with three leaflets (far right).

DETAILED DESCRIPTION

Figure 1:
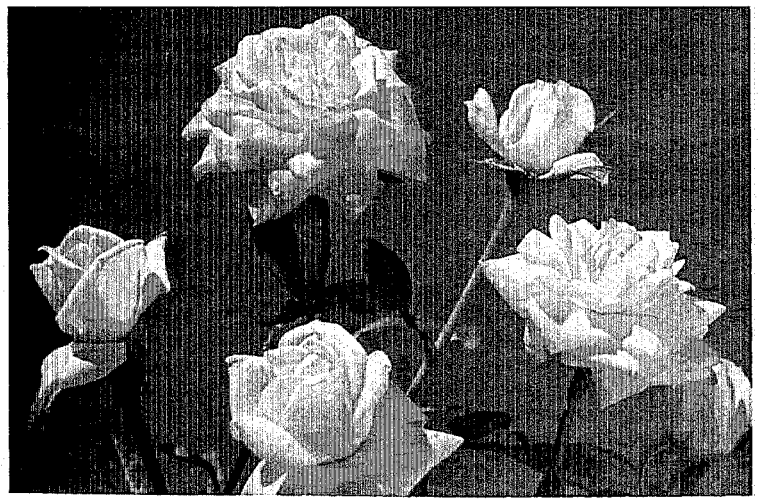
Figure 2:
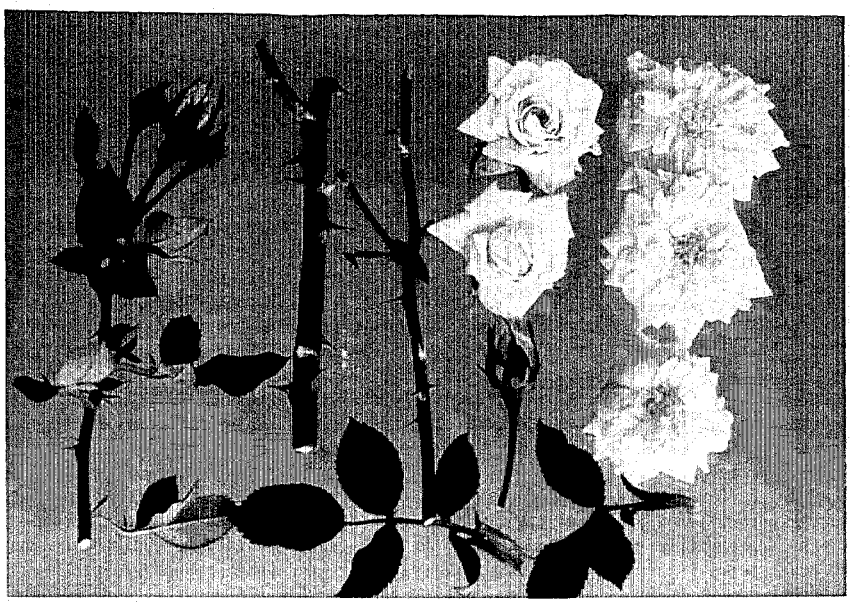

The plants described were grown outdoors during June at West Grove, Pa.

The chart utilized in the identification of the colors is that of The Royal Horticultural Society (R.H.S. Colour Chart).

Class: Miniature.

Plant:

*Height.*—Approximately 25 to 45 cm. on average.

*Bearing.*—Semi-erect.

Branches:

*Color.*—*Young stems: light green, Yellow-Green Group* 144C, with reddish shading. Mature wood: medium green, Green Group 137C.

*Thorns.*—Shape of upper edge: straight. Shape of lower edge: concave, slightly recurved toward the cane. Size: medium to small. Quantity: Average. Color on young stems: deep red. Color on mature wood: becomes paler, but retaining reddish tint.

Foliage:

*Stipules.*—Linear, occasionally leaf-like, usually approximately 2 to 3 cm. in length, but sometimes up to 4½ cm. in length, serrulate with red edge.

*Petiole.*—Inner surface: lightly grooved, reddish green (young leaves), and medium green with red edge (mature leaves), smooth with glandular edges. Outer surface: light green (mature leaves) or with reddish cast (young leaves), glandular with no prickles.

*Leaflets.*—Number: 3 or 5 (most common). Shape: ovate with rounded base, approximately 2 to 3 cm. in length on average, approxiamtely 1 to 2 cm. in width on average. Teeth: regular and serrulate. General effect: leaves ample, dense and glossy.

*Color.*—Young leaves: Upper surface: dark green, Yellow-Green Group 144A, with light bronze shading. Lower surface: medium green with bronze cast. Mature leaves: Upper surface: dark green, Green Group 137A with thin red edge. Lower surface: medium green, Green Group 138B.

Flowers:

*Number of flowers.*—Commonly pauciflorous, but will vary between one and eight flowers per stem.

*Peduncle.*—Straight, semi-rigid, medium green with bronze tint, bears a moderate amount of reddish prickles, approximately 3 to 4 cm. in length on average.

*Sepals.*—Inner surface: medium green with light red mid-rib, tomentose. Outer surface: dark green with red tips, edge is serrate with occasional spurs, generally glandular.

*Bud.*—Shape: oblong. Length: approximately 1.5 to 2 cm. on average at opening of the sepals. Color as sepals open-outer side of petals: Orange Group 29B at petal apex with edges speckled with Red Group 40C. The orange areas blend to Yellow Group 6C at the base of the petals and Yellow Group 6B at the point of petal attachment. Color as sepals open-inner side of petals: Orange Group 33A at petal apex blending to Yellow Group 6B at the base of the petals and at the point of petal attachment. Color when one-half open-outer side of petals: Red Group 39B at petal apex with petal side margins blending to Yellow Group 6D at the petal base and ending with Yellow Group 6C at the point of petal attachment. Color when one-half open-inner side of petals: Orange Group 33A at petal apex blending to Yellow Group 6D at the petal base and ending with Yellow Group 6C at the point of petal attachment.

*Flower.*—Shape: moderately high center, petals generally notched. Diameter: approximately 3.5 to 5.5 cm. on average. Color when fully open-inner side of petals: Red Group 39B at petal apex and margins blending to Yellow Group 6D at the petal base and ending with Yellow Group 6B at the point of petal attachment. Color prior to petal drop-inner side of petals: Red Group 38B at petal apex and petal margins blending to Yellow Group 4D at the petal base and ending with Yellow Group 6C at the point of petal attachment. Fragrance: very light. Lasting quality: long. Texture: firm. Petal shape: obovate, occasionally obcordate, with claw which is barium yellow, Yellow Group 10A. Number of petals: approximately 45 on average. Stamens: approximately 40 on average, anthers commonly are ochre colored. Pistils: approximately 54 on average, stigmas are normal, and yellowish in coloration.

Development:

*Vegetation.*—Vigorous and regular.

*Flowering.*—Very abundant, repeats well.

*Capacity for bearing fruit.*—Good.

*Resistance to frost.*—Average for class.

*Resistance to diseases.*—Average for class.

I claim:

1. A new and distinct variety of Miniature rose plant, substantially as illustrated and described, wherein:

(a) from the physical standpoint the plant with medium green adult wood has a semi-erect growth habit, forms dark green glossy leaves, and forms double flowers which exhibit a blend of orange and yellow tones with a pinkish accent at the flower center; and (b) from the biological standpoint the plant has vigorous and regular vegetation, exhibits an abundant and repeated florescence, exhibits the ability to grow well in the greenhouse or outside, possesses the ability for its blossoms to last for a long time, and forms petals which detach cleanly.

* * * * *